(12) United States Patent
Phanstiel, IV (10) Patent No.: US 8,410,311 B1
(45) Date of Patent: Apr. 2, 2013

(54) FLUORESCENT CYTOTOXIC COMPOUNDS SPECIFIC FOR THE CELLULAR POLYAMINE TRANSPORT SYSTEM

(75) Inventor: Otto Phanstiel, IV, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 367 days.

(21) Appl. No.: 12/754,962

(22) Filed: Apr. 6, 2010

Related U.S. Application Data

(63) Continuation-in-part of application No. 12/113,540, filed on May 1, 2008.

(60) Provisional application No. 60/166,889, filed on Apr. 6, 2009.

(51) Int. Cl.
C07C 211/00 (2006.01)
A61B 5/00 (2006.01)
A61B 8/00 (2006.01)
A61B 10/00 (2006.01)

(52) U.S. Cl. ......................................... 564/305; 424/9.6

(58) Field of Classification Search .................. None
See application file for complete search history.

(56) References Cited

PUBLICATIONS

Gardner et al. J. Med. Chem 2004, 47, 6055-6069.*
Kaur et al. J. Med. Chem. 2008, 51, 1393-1401.*

* cited by examiner

Primary Examiner — Sudhakar Katakam
Assistant Examiner — Clinton Brooks
(74) Attorney, Agent, or Firm — Timothy R. Van Dyke; Beusse, Wolter, Sanks, Mora & Maire, PA

(57) ABSTRACT

Cyano-substituted anthracene containing polyamines were synthesized and shown to be efficient polyamine transporter ligands. Moreover, these compounds (3 and 4) had improved fluorescence properties over previously known anthryl-polyamine conjugates, which facilitated their intracellular trafficking by confocal microscopy. These cytotoxic fluorescent agents may find use as molecular probes which traffic into cells via the polyamine transport system and may also be viable anticancer drugs which are readily quantified in human tissues due to their excellent fluorescence properties: (excitation: λ 405 nm) and emission (420 nm) occurs in the visible light range. The ability to excite and emit in the visible range provides an advantage to these probes as these wavelengths are not toxic to human cells (versus ultraviolet mediated excitations, λ<400 nm) and visible light lasers are less costly to purchase and operate than UV laser sources.

8 Claims, 6 Drawing Sheets

1: Compound Ant44

2: Compound 44-Ant44

3: "cyano-Ant44"

4: "cyano-44-Ant44"

REACTION SCHEME 3

FIG. 4

REACTION SCHEME 4

FLUORESCENT CYTOTOXIC COMPOUNDS SPECIFIC FOR THE CELLULAR POLYAMINE TRANSPORT SYSTEM

RELATED APPLICATION

This application claims priority from co-pending provisional application Ser. No. 60/166,889 which was filed on 6 Apr. 2009, and is also a continuation-in-part of application Ser. No. 12/113,540 filed on 1 May 2008, both applications being incorporated herein by reference in their entirety.

FIELD OF THE INVENTION

The present invention relates to the field of mammalian cellular physiology and, more particularly, to fluorescent molecules that are transported into a cell via the polyamine transporter system.

BACKGROUND OF THE INVENTION

Polyamines are organic compounds having at least two primary amine groups, for example $NH_2$. These compounds have a role in the metabolism of mammalian cells but their exact functions are not well described. It is known that cells can synthesize polyamines and that, if cellular synthesis is blocked, exogenously supplied polyamines may be imported into the cell via the so called polyamine transporter system.

While it is known that polyamines are synthesized in cells through highly-regulated pathways, their actual function has not been fully elucidated.

They are known to bind to DNA as cations, and, in structure, they represent compounds with cations that are found at regularly-spaced intervals (unlike, say, $Mg^{++}$ or $Ca^{++}$, which are isolated point charges).

When synthesis of cellular polyamines is inhibited, the cell's growth is stopped or severely inhibited. Adding exogenous polyamines reactivates the growth of these cells. Most eukaryotic cells have a polyamine transporter system on their cell membrane that facilitates the intake of exogenously provided polyamines. The polyamine transporter (PAT) system is highly active in rapidly proliferating cells and is the target of some chemotherapeutics currently under development.

Polyamines are also known to modulate a number of ion channels, to enhance permeability of the blood-brain barrier and to even regulate senescence in plants, thus being considered plant hormones. Since many cancer cell lines have active polyamine transporters, it is possible to target these cells using the molecular recognition events involved in polyamine import.

SUMMARY OF THE INVENTION

With the foregoing in mind, the present invention advantageously provides novel fluorescent compounds that are rapidly internalized by a cell via the polyamine transporter system, thus providing easily tracked probes for the further study of this transport mechanism. Consequently, it may be possible to attach a therapeutic drug moiety to the presently disclosed fluorescent PAT probes to provide the unique ability of tracking the drug into the cell by visualizing the fluorescent tag.

Figure 1:
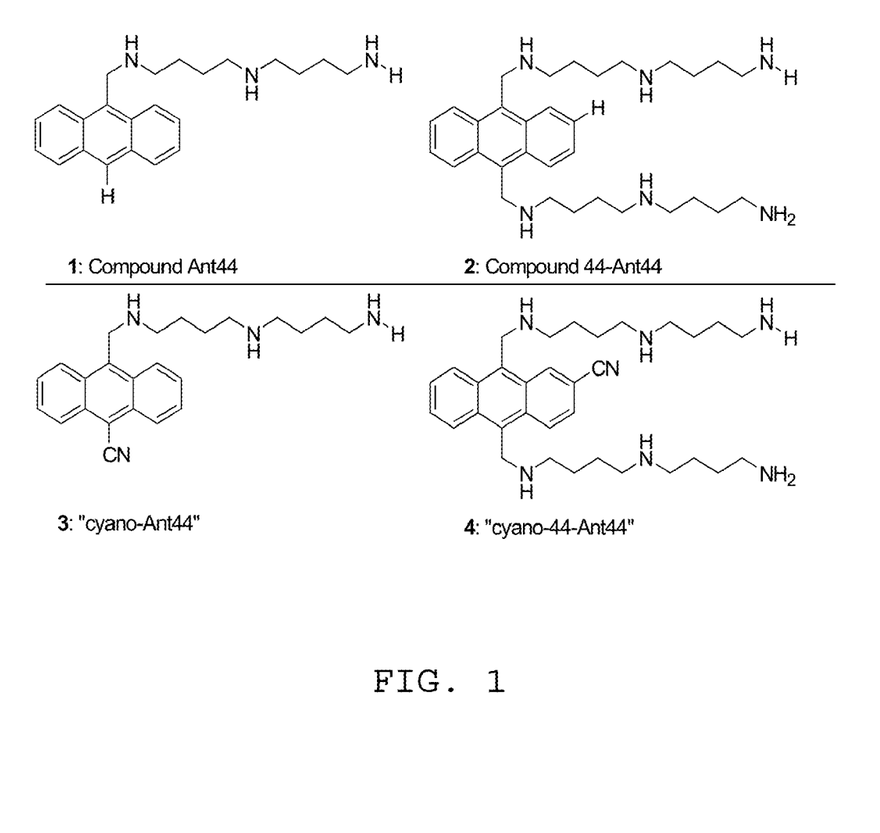
FIG. 1 provides the formulas for previously known compounds 1-2, as well as presently disclosed novel compounds 3-4 according to an embodiment of the present invention.

After studying polyamine transport processes for many years, we discovered and have previously disclosed compounds 1 and 2 as optimal polyamine transporter (PAT) selective agents (FIG. 1). These compounds enter and kill cells via their polyamine transport system. The polyamine transport system is a measurable phenomenon but the genes and proteins involved are poorly understood. The instant invention couples our earlier discovery of PAT selective agents 1 and 2 and modifies their structure to now provide compounds 3 and 4, which are highly fluorescent compounds useful for tracking polyamine uptake processes in mammalian systems (FIG. 1).

We have synthesized these fluorescent probes (compounds 3 and 4) and performed some confocal microscopy with compound 3 to illustrate this technology in action. An important improvement over earlier systems is that even though compounds 1 and 2 are fluorescent they require excitation in the ultraviolet range (393 nm) and emit in the visible range (410 nm). This requirement is detrimental to biological studies as the UV radiation is injurious and can kill the exposed cells.

New compounds 3 and 4 contain a cyano group which extends the compounds' pi system just enough that these systems are now excited at 405 nm (blue light) and emit at 420 nm (in the visible light range). This improvement in their photophysical properties coupled with their high selectivity in entering cells via the PAT system make these compounds valuable new tools for molecular and cell biologists interested in tracking polyamine uptake phenomena via fluorescence measurements or via confocal microscopy.

The present disclosure also contemplates that the invention includes the compound of Formula 3 used in manufacturing a pharmaceutical composition acceptable for administration to a patient. Those skilled in the art should recognize that the compounds of this invention may be administered to mammals, preferably humans, either alone or in combination with pharmaceutically acceptable carriers, excipients or diluents, in a pharmaceutical composition, according to standard pharmaceutical practice. The compounds can be administered by any route but are preferably administered parenterally, including by intravenous, intramuscular, intraperitoneal, subcutaneous, rectal and also by topical routes of administration.

The term "composition" is intended to encompass a product comprising the disclosed compounds in amounts effective for causing the desired effect in the patient, as well as any product which results, directly or indirectly, from combination of the specific ingredients. However, the skilled should understand that when a composition according to this invention is administered to a human subject, the daily dosage of active agents will normally be determined by the prescribing physician with the dosage generally varying according to the age, weight, sex and response of the individual patient, as well as the severity of the patient's symptoms.

The terms pharmaceutical composition, pharmaceutically and/or pharmacologically acceptable for administration to a patient refer to molecular entities and/or compositions that do not produce an adverse, allergic and/or other untoward reaction when administered to a subject, be it animal or human, as appropriate. As known to the skilled, a pharmaceutically acceptable composition or carrier includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For administration, preparations should meet sterility, pyrogenicity, general safety and/or purity standards as required by FDA Office of Biologics standards. The skilled will find additional guidance in preparation of pharmaceutically acceptable compositions by consulting United States Pharmacopeia (USP) or other similar treatises employed in the pharmaceutical industry.

The present disclosure also contemplates a second compound, of Formula 4 and related to the compound of Formula 3 by both being derivatives of an anthracene compound. This second compound is shown below according to Formula 4 and salts thereof. The compound of Formula 4 has chemical and biological properties that parallel those of the compound of Formula 3 and may be employed in a likewise manner, as described above.

As used herein, the terms "treat," "treating" or "method of treatment" refer to both therapeutic treatment and prophylactic or preventive measures, wherein the object is to prevent or slow down (lessen) an undesired physiological change or disorder, such as the development or spread of cancer or other proliferation disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with a compound of the invention may include reduction of undesirable cell proliferation, and/or induction of apoptosis and cytotoxicity. "Treatment" can also mean prolonging survival as compared to expected survival if not receiving treatment.

The terms "effective to inhibit" or "growth inhibitory amount" of the compounds of the invention refer to an amount which reduces (i.e., slows to some extent and preferably stops) proliferation of a target cell, such as a tumor cell, either in vitro or in vivo, irrespective of the mechanism by which cell growth is inhibited (e.g., by cytostatic properties, cytotoxic properties, etc.).

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

U.S. patent application Ser. No. 12/113,540 was filed on 1 May 2008 and application Ser. No. 12/113,970 was filed on 2 May 2008. These two applications disclosed other polyamine compounds related to and having similar biological properties to the presently disclosed compounds 3 and 4. Accordingly, these two patent applications are incorporated herein by reference in their entireties.

In the present disclosure, using Chinese hamster ovary (CHO) cells as a test cell line, we have shown that compound 3 is significantly more toxic to wild-type CHO cells than to their CHOMG mutant, which is defective in polyamine transport. Since these compounds use the PAT for cellular entry, they are very toxic to cell lines containing active polyamine transporters (e.g., CHO cells) but less so to cell lines with defects in this pathway (CHOMG).

As known to those skilled in the art, the $IC_{50}$ is the concentration of the drug required to kill 50% of the relative cell population. That is, the lower the $IC_{50}$, the more potent the drug. See Table 1. We employed confocal microscopy to look at the cell localization behavior of compound 3 in these two cell lines at different time points.

Figure 2:
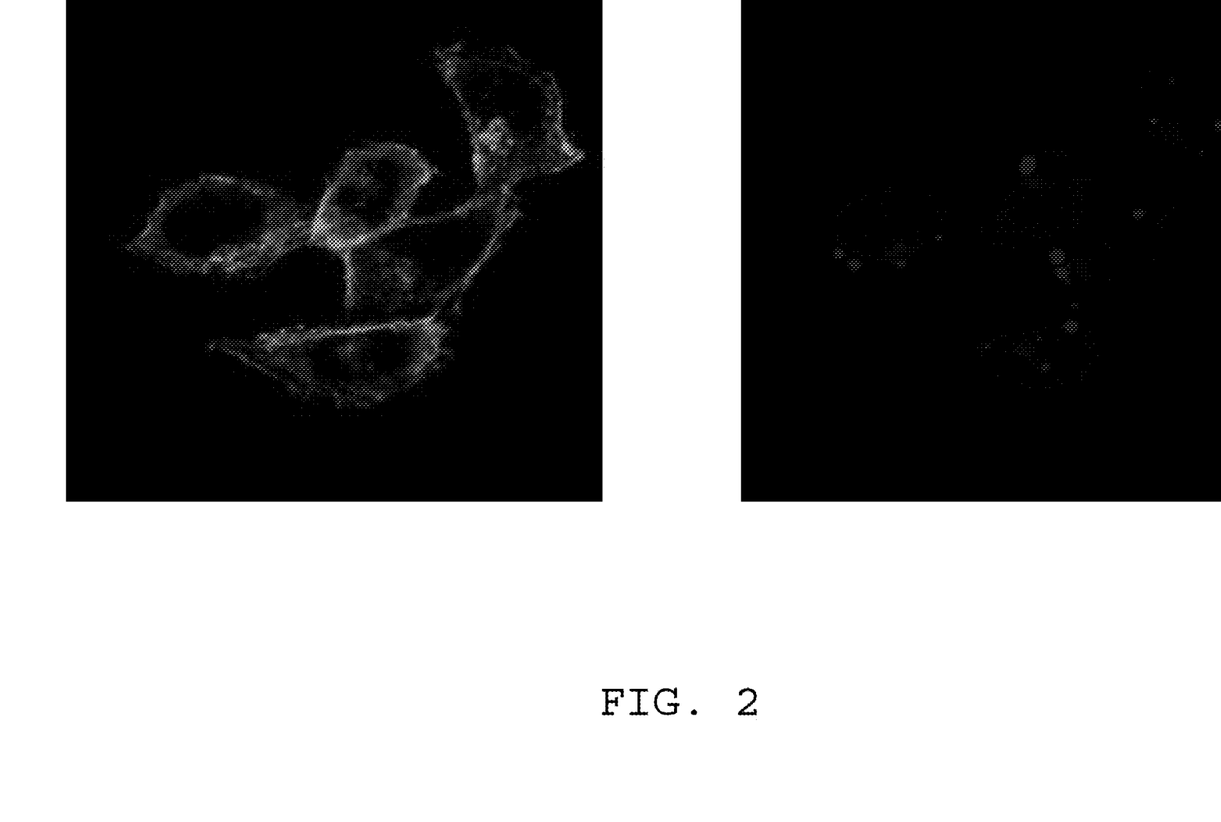
FIG. 2 shows a fluorescence microscopy view of PAT inactive CHOMG cells treated with compound 3 (10 μM) after 4 hours.

FIG. 2 shows inactive CHOMG cells treated with compound 3 (10 uM), the fluorescence microscopy view being taken after the cells had been exposed to the compound for 4 hrs. Compound 3 is mainly sequestered in intracellular vesicles at the 4 hr incubation time-point (FIG. 2). The CHOMG mutant defect seems to block vesicular escape of the probe. Note that the fluorescent probe, compound 3, appears as a blue dot (right image) as it remains localized within vesicles. The green image (left image) is acquired from an actin-binding stain to show the cells' cytoskeletal architecture surrounding the blue probe 3.

Figure 3:
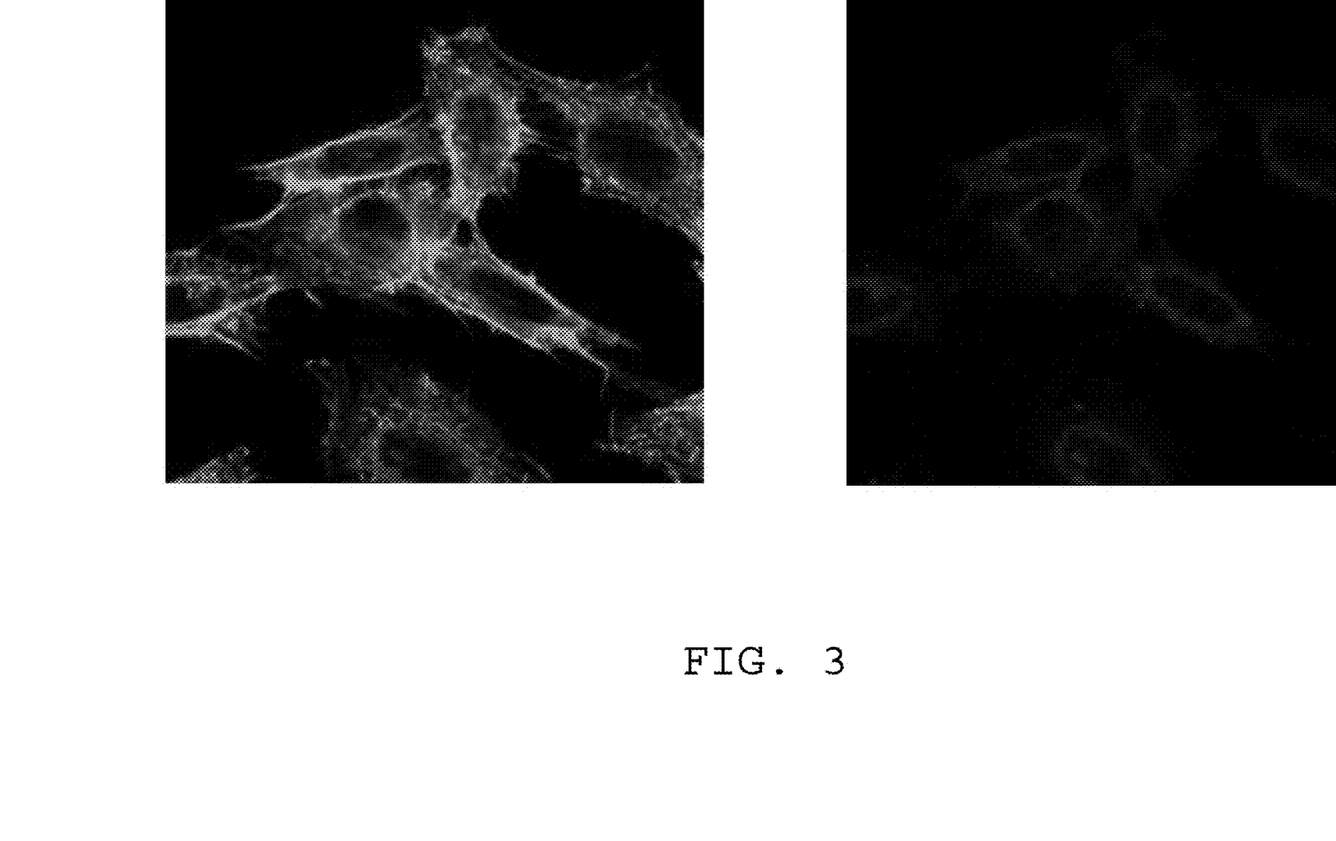
FIG. 3 again shows a fluorescence microscopy view of CHO wild type cells treated with compound 3 (10 μM) after 4 hours.
Figure 4:
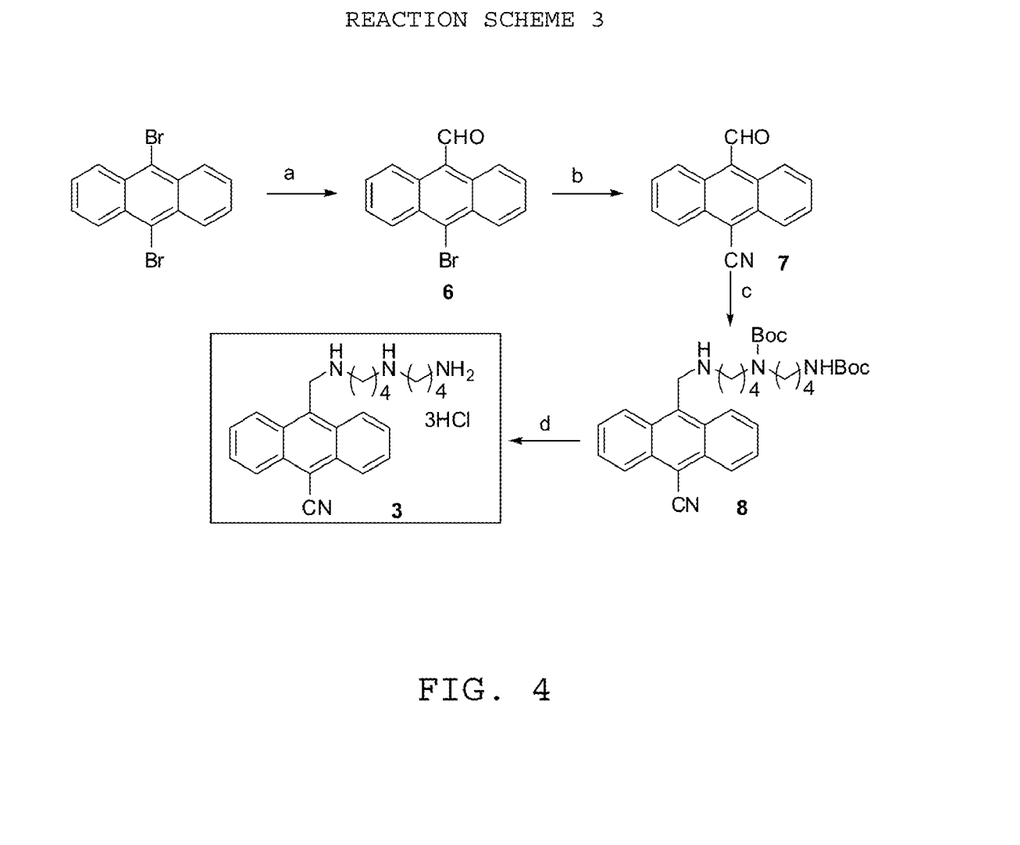
FIG. 4 illustrates a synthetic scheme for producing compound 3 (Reaction Scheme 1), wherein reagents are a) BuLi, DMF, b) Pd(OAc)$_2$/K$_4$[Fe(CN)$_6$], c) $_{H_2N}$(CH$_2$)$_4$N(Boc)(CH$_2$)$_4$ NHBoc, NaBH$_4$, and d) 4 N HCl.
Figure 5:
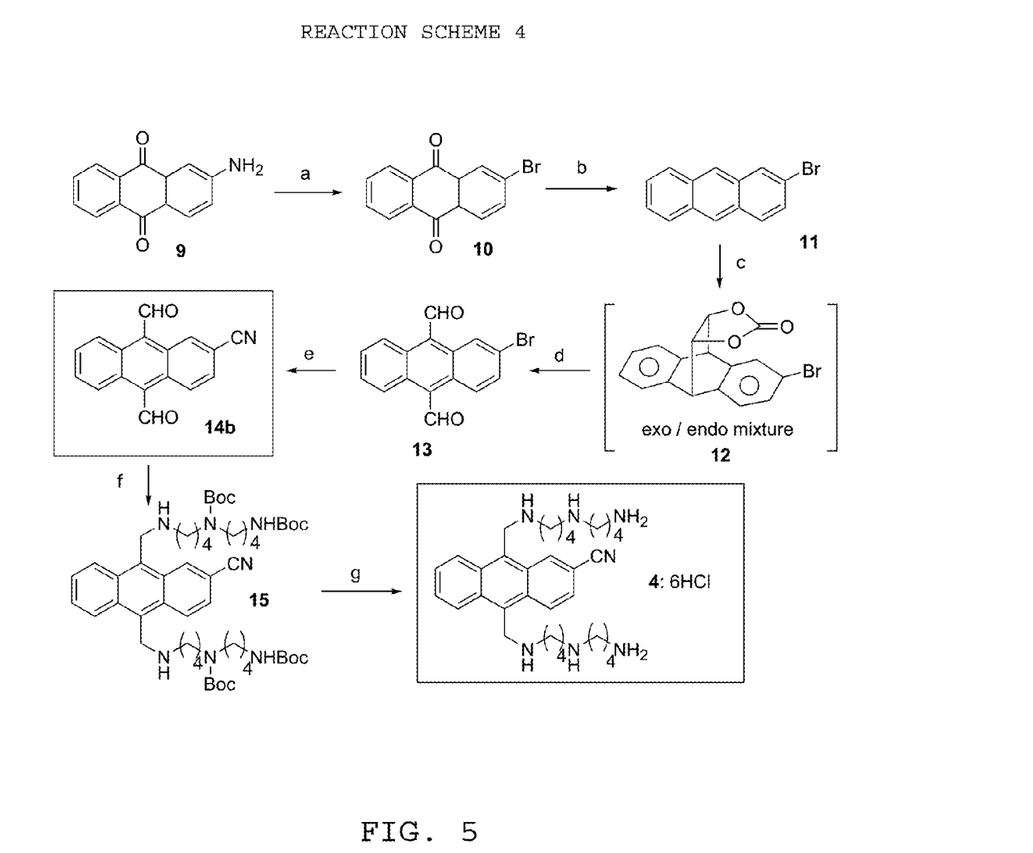
FIG. 5 depicts a synthetic scheme for producing compound 4 (Reaction Scheme 2), wherein reagents employed are (a) CuBr$_2$/t-BuONO; (b) NaBH$_4$, then 3 M HCl; (c) vinylene carbonate, d) KOH/EtOH to give the diol, then Pb(OAc)$_4$; (e) Pd(OAc)$_2$/K$_4$[Fe(CN)$_6$]; (f) H$_2$N(CH$_2$)$_4$N(Boc)(CH$_2$)$_4$NHBoc, NaBH$_4$, and (g) 4 N HCl.

In FIG. 3 PAT active CHO wild type cells are shown after being treated with compound 3 (10 uM) for 4 hrs. In contrast to CHOMG, shown in FIG. 2, the wild type CHO cells shown in FIG. 3 allow compound 3 to escape the vesicle compartments and arrive at the perinuclear compartment after 4 hrs. of incubation. This is clearly seen as the 'blue halo' effect. Note that the fluorescent drug, compound 3, appears as a blue image. The green image is taken with an actin-binding stain to show the cells' cytoskeletal architecture.

The skilled will recognize that the CHOMG/CHO $IC_{50}$ ratio is indicative of PAT selectivity. As seen in Table 1, control compound 5 (a water soluble anthracene derivative with the incorrect message to utilize the polyamine transporter, PAT) gave the same $IC_{50}$ value in both the CHO and CHOMG cell lines. i.e. the CHOMG/CHO $IC_{50}$ ratio=1. Therefore, the control compound 5 had no selectivity for targeting cells with the active PAT. In contrast, the smart polyamine probes 1-4 all showed greater toxicity to the CHO cell line over its CHOMG mutant (IC50 ratios>>1). In addition, the L1210 cells (murine leukemia cells) were more sensitive (lower $IC_{50}$ values) to the smart probes 1-4 than the control 5. These cells also gave lower $K_i$ values, which is indicative of greater binding to the PAT. In contrast the control 5 gave a significantly higher $K_i$ value (32.2 μM).

Figure 6:
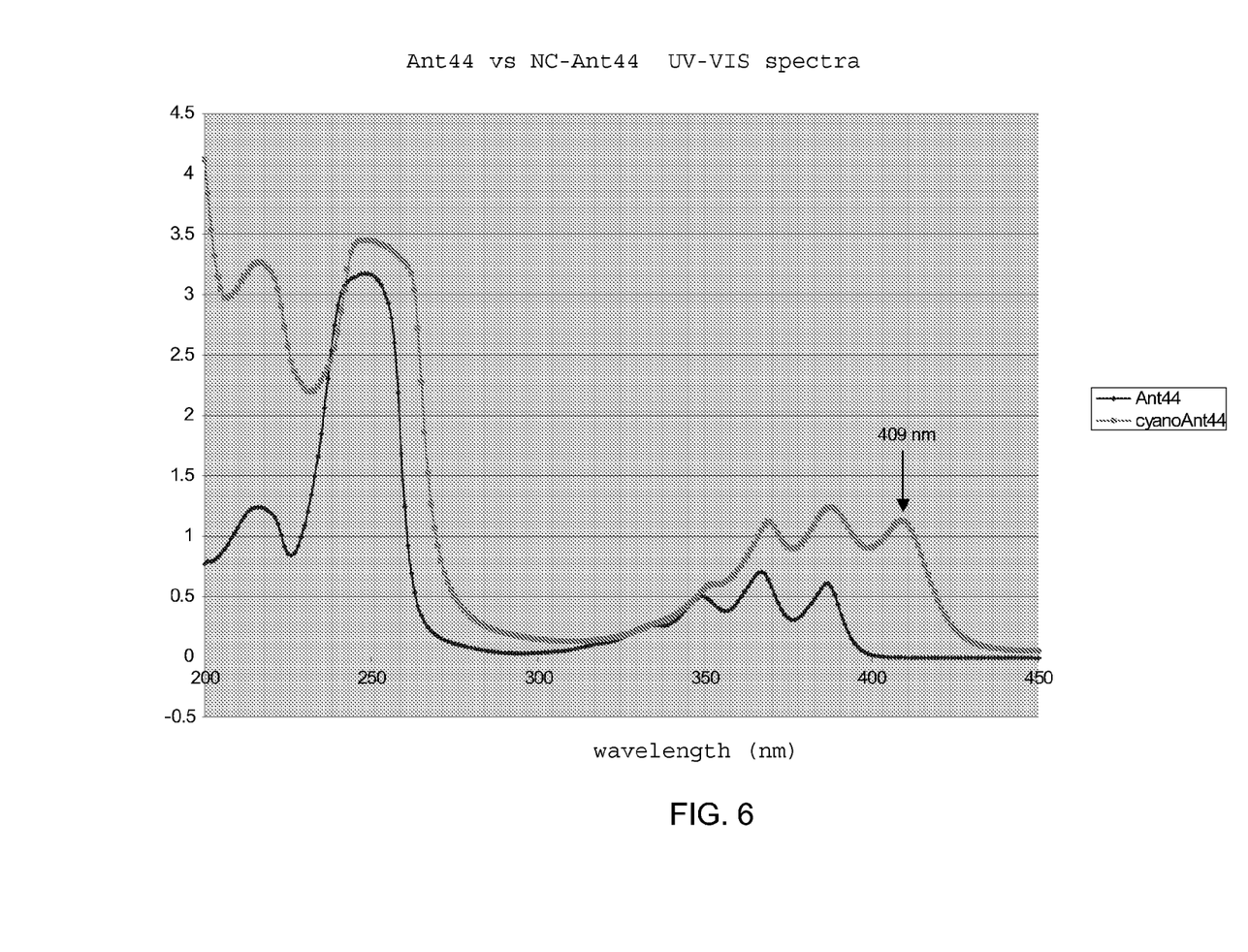
FIG. 6 shows a line graph depicting the UV-VIS spectra of Ant44 (compound 1) and cyanoAnt44 (compound 3) in PBS buffer, 100 μM at 25° C.

A comparison of the UV-visible absorbance spectra of the Ant44 (compound 1) and cyanoAnt44 (compound 3) derivatives (FIG. 6) shows a shift to longer wavelength (red shift) of the absorbance spectrum upon cyanation of the ring. The extended pi system is responsible for this shift to 409 nm and was part of the design process in constructing the cyano derivative.

An important reason for using >400 nm for polyamine probe excitation is that one can use a visible light laser, for example a blue laser, to excite the compound at 405 nm. In contrast, exciting probes of wavelength below 400 nm would require a very costly UV laser, which are also expensive to maintain and to cool during operation.

In addition, UV excitation has other problems since other biofluorophores such as DNA bases, tryptophan, etc., can be excited by UV radiation. Accordingly, in order to distinguish the presently disclosed polyamine probes it was advantageous to be able to use excitation

TABLE 1

Biological Evaluation of polyamine derivatives in CHO and CHO-MG cells

1: x=1, y=4, z=4; R=H; X=H
3: x=1, y=4, z=4; R=H; X=CN

2: x=1, y=4, z=4; X=H
4: x=1, y=4, z=4; X=CN

5: x=1, y=4

| Compd (tether) | CHO-MG $IC_{50}$ in μM | CHO $IC_{50}$ in μM | (CHO-MG/CHO) $IC_{50}$ Ratio[b] | L1210 $K_i$ value in μM | L1210 $IC_{50}$ value in μM |
|---|---|---|---|---|---|
| 1: Ant-4,4 | 66.7 (±4.1) | 0.45 (±0.10) | 148 | 1.8 (±0.1) | 0.3 (±0.1) |
| 2: 4,4-Ant-4,4 | >100 | 0.045 (±0.003) | >2222 | 0.39 (±0.05) | 0.78 (±0.07) |
| 3: cyano-Ant-4,4 | 48.7 (±1.6) | 0.96 (±0.01) | 51 | 3.8 (±0.28) | 0.31 (±0.01) |
| 4: cyano-4,4-Ant-4,4 | ND | ND | ND | ND | ND |
| 5: Ant-4 (control) | 7.6 (±0.4) | 7.7 (±0.5) | 1 | 32.2 (±4.3) | 6.3 (±0.3) |

[a]Cells were incubated for 48 h with the respective conjugate, Ant = anthrylmethyl;
[b]a measure of PAT selectivity, not determined frequencies in the visible light region. We accomplished this by making the cyano derivatives which have an absorption band near 409 nm in PBS (see FIG. 6).

Materials and Methods

Control compounds 1, 2, and 5 were synthesized previously. REF: (a) "Synthesis and Biological Evaluation of N[1]-(anthracen-9-ylmethyl)triamines as Molecular Recognition Elements for the Polyamine Transporter," Wang, C.: Delcros, J-G.; Biggerstaff, J.; Phanstiel IV, O. *J. Med. Chem.* 2003, 46, 2663-2671; (b) A Comparison of Chloroambucil- and Xylene-containing polyamines leads to improved ligands for accessing the polyamine transporter. Navneet Kaur, Jean- Guy Delcros, and Otto Phanstiel IV. *J. Med. Chem.* 2008, 51, 1393-1401; (c) "N'-Substituent Effects in the Selective Delivery of Polyamine-Conjugates into Cells Containing Active Polyamine Transporters" Gardner, R. A.; Delcros, J-G.; Konate, Breitbeil III, F.; Martin, B.; Sigman, M.; Huang, M.; Phanstiel IV, O. *J. Med. Chem.* 2004, 47, 6055-6069.)

10-((4-(4-aminobutylamino)butylamino)methyl)anthracene-9-carbonitrile (3):

The diBOC amine 8 (0.15 mmol) was dissolved in EtOH (3 mL) and cooled to 0° C. 4N HCl (6 mL) was added dropwise at 0° C. The solution was stirred at it overnight. The solution was concentrated under reduced pressure to give a yellow solid 3 in 96% yield. $^1$H NMR (300 MHz. $D_2O$): δ 8.18 (d, 2H), 8.00 (d, 2H), 7.73 (m, 4H), 5.06 (s, 2H), 3.25 (t, 2H), 3.06 (m, 6H), 1.75 (m, 8H). d HRMS: theory for $C_{24}H_{30}N_43HCl$: 375.2543. found 375.2553. Anal. calcd for $C_{24}H_{33}N_4Cl_30.2H_2O$: C, 59.13; H, 6.91; N, 11.49. Found: C, 59.21; H, 7.01; N, 11.54.

9-Bromo-10-anthracenecarboxaldehyde (6):

To the yellow suspension of 9,10-Dibromoanthracene (2 g, 5.95 mmol) in THF (20 mL) at −90° C., n-BuLi (2.88 mL, 7.18 mmol, 2.5 M in hexane) was added dropwise. Orange solution was observed after 45 min additional stirring. Anhydrous DMF (0.92 mL, 11.9 mmol) was added to the orange solution. The reaction mixture was slowly warmed to room temp and stirred overnight. The reaction mixture was quenched with $H_2O$ and extracted with $CH_2Cl_2$. The organic layer was washed with 10% aq. $Na_2CO_3$ solution (3×50 mL). The $CH_2Cl_2$ layer was separated, dried over anhydrous $Na_2SO_4$, filtered and removed in vacuo to give yellow solid. The crude product was purified by column chromatography using 30% $CH_2Cl_2$/hexane to give 6 in 68% yield. $R_f$=0.3 (30% $CH_2Cl_2$/hexane; $^1$H NMR (CDCl$_3$) d 11.39 (s, 1H), 8.77-8.82 (d, 2H), 8.55-8.60 (d, 2H), 7.56-7.67 (m, 4H). (Ref. de Montigny, Frederic; Argouarch, Gilles; Lapinte, Claude. New route to unsymmetrical 9,10-disubstituted ethynylanthracene derivatives. *Synthesis*, 2006, 2, 293-298.)

9-Cyano-10-anthraldehyde (7):

9-Bromo-10-anthracenecarboxaldehyde (200 mg, 0.7 mmol) was heated with copper (I) cyanide (75.4 mg, 0.84 mmol) and pyridine (3 mL) for 12 hr at 230° C. After cooling, the mixture was washed with dilute NH$_4$OH and ether. The ether extract was washed with water, 1N HCl, again water, dried over anhydrous $Na_2SO_4$, filtered and removed in vacuo to give yellow solid, which was purified using column chromatography using 40% $CH_2Cl_2$/hexane in 40% yield. $^1$H NMR (CDCl$_3$) δ 11.43 (s, 1H), 8.72-8.77 (d, 2H), 8.44-8.49 (d, 2H), 7.71-7.77 (m, 4H); $^{13}$C NMR (CDCl$_3$) δ 193.4, 160.8, 129.9, 129.4, 129.0, 126.3, 124.4. (Ref. Gore, P. H.; Gupta, S. D.; Obaji, G. A. Anomalous reactions of cyanide with two hindered aromatic aldehydes. *Journal fuer Praktische Chemie* (Leipzig). 1984, 326, 381-4.)

Optimized Procedure:

DMAC (N,N-dimethylacetamide) was used as a solvent. As reaction is oxygen sensitive, DMAC was placed in three necked round bottom flask with three way stopcock with vacuum line in one side and ultra dry $N_2$ balloon on the other side. Evacuation of the flask was done and DMAC was kept under $N_2$ environment. To three necked flask Bromoaldehyde 6 (25 mg, 0.088 mmol), Zn(CN)$_2$ (18.5 mg, 0.157 mmol), Pd$_2$(dba)$_3$ (2.09 mg, 0.002 mmol), Zn dust (1 mg, 0.022 mmol) were weighed out and flask was evacuated and $N_2$ was allowed to enter the flask via three way stopcock. DMAC (4 mL) was added to the flask via a syringe keeping the flask under vacuum. t-Butyl phosphine (1.77 mg, 0.009 mmol) was added via syringe. The whole assembly was transferred in an oil bath at 80° C. and let the reaction stir at 80° C. for three hours. After monitoring the consumption of 6 by TLC (40% $CH_2Cl_2$/Hexane), EtOAc (20 mL) was added to the reaction mixture and crude reaction mixture was washed with saturated solution of $K_2CO_3$, organic layer was again washed with saturated solution of NH$_4$Cl. The EtOAc layer was dried over anhydrous $Na_2SO_4$, filtered and removed in vacuo to give yellow solid 7 in 89% yield by NMR.

(4-tert-Butoxycarbonylamino-butyl)-{4-[(10-cyano-anthracen-9-ylmethyl)-amino]-butyl}-carbamic acid tert-butyl ester (8):

To a stirred solution of $N^1,N^5$-di-Boc homospermidine (92 mg, 0.26 mmol) in 25% MeOH/$CH_2Cl_2$ (10 mL), was added a solution of 9-Cyano-10-anthraldehyde 7 (49 mg, 0.21 mmol) in 25% MeOH/$CH_2Cl_2$ (10 mL) under $N_2$. The mixture was stirred at room temperature overnight until the imine formation was complete (monitored by NMR). The solvent was removed in vacuo, the solid residue dissolved in 50% MeOH/$CH_2Cl_2$ (20 mL) and the solution cooled to 0° C. NaCNBH$_3$ (0.25 mmol) was added in small portions to the solution and the mixture was stirred at it overnight. The solvent was removed in vacuo, the solid residue dissolved in $CH_2Cl_2$ (30 mL) and washed with $Na_2CO_3$ solution (10% aq. 3×30 mL). The $CH_2Cl_2$ layer was dried over anhydrous $Na_2SO_4$, filtered and removed in vacuo to give an oily residue. The oil was purified by flash column chromatography (1.5% MeOH/$CH_2Cl_2$) to yield the product as a pale yellow solid (93 mg, 73%), $R_f$=0.23 (3% MeOH/0.5% NH$_4$OH/$CH_2Cl_2$); $^1$H NMR (300 MHz, CDCl$_3$) δ 8.38 (m, 4H), 7.64 (m, 4H), 4.70 (s, 2H), 3.12 (m, 6H), 2.89 (m, 2H), 1.41-1.56 (m, 26H): $^{13}$C NMR: δ 156.0, 155.6, 139.1, 133.1, 129.6, 128.5, 127.0, 126.2, 125.1, 117.5, 79.4, 53.7, 50.6, 46.9, 46.1, 40.4, 28.7, 27.7, 26.1. HRMS (FAB) m/z calcd. for $C_{34}H_{46}N_4O_4$ (M+H)$^+$ 575.3592. found 575.3591. Anal. calcd for $C_{34}H_{46}N_4O_4.1H_2O$: C, 68.89; H, 8.16; N, 9.45. Found: C, 68.77; H, 8.02; N, 9.42.

2-Bromoanthraquinone (10):

Copper (II) bromide (35.0 g, 0.157 mol, 3.76 equiv.) was dissolved in freshly-distilled acetonitrile (200 mL) at room temperature to form an opaque dark-green solution. tert-Butyl nitrite (15 mL, 12.9 g, 0.125 mol, 1.49 equiv.) was added at 0° C. and stirred for 30 minutes at 0° C. 2-Aminoanthraquinone 9 (18.60 g, 0.0834 mol, 1 equiv.) was dissolved in tetrahydrofuran (THF, 300 mL) at room temperature to form an opaque red-brown solution. The 2-aminoanthraquinone 9 solution was quickly added to the copper (II) bromide solution at 0° C. and the solution was stirred for 2 hours at 0° C. with venting of the nitrogen gas by-product every 5 minutes until the bubbling ceased. The consumption of 2-aminoanthraquinone 9 was monitored by thin-layer chromatography (100% CHCl$_3$, $R_f$=0.32). Once the 2-aminoanthraquinone 9 was consumed, the THF and acetonitrile solvents were removed from the mixture via rotary evaporation to give a brown and black solid residue. The solid was rinsed with deionized water to form a suspension. The resulting slurry was vacuum filtered and rinsed with deionized water. The filtration receiving flask was changed and the solid was washed with $CH_2Cl_2$ through the filter paper, leaving a red-brown solid by-product and forming a yellow-brown solution. The $CH_2Cl_2$ was removed from the solution via rotary evaporation, leaving a yellow solid consisting of the product 2-bromoanthraquinone 10 and by-product anthraquinone. The desired product was separated and purified from the unwanted by-product through column chromatography (35% CHCl$_3$/hexane, $R_f$=0.33 and $R_f$=0.28 respectively), providing 2-bromoanthraquinone 10 as a light yellow solid (11.2 g;

37%). $^1$H NMR (CDCl$_3$): δ 8.42 (d, 1H), 8.30 (m, 2H), 8.16 (d, 1H), 7.91 (dd, 1H), 7.80 (m, 2H).

2-Bromoanthracene (11):

2-Bromoanthraquinone 10 (8.50 g, 0.0296 mol, 1 equiv) and a 50:50 mixture of isopropyl alcohol and tetrahydrofuran (200 mL) were stirred for 10 minutes at 0° C. forming a yellow suspension. NaBH$_4$ (6.70 g, 0.177 mol, 6.0 equiv.) was added to the suspension at 0° C. The mixture was stirred at 0° C. for three hours, turning red in color. The solution was then warmed to room temperature. Additional NaBH$_4$ (3.35 g, 0.089 mol, 3.0 equiv.) was added to the solution at room temperature and the solution was stirred at room temperature for 12 hours, turning into an orange suspension. Deionized water (10 mL) was added to the solution at room temperature and the solution was stirred at room temperature for an additional 12 hours. The consumption of 2-bromoanthraquinone 10 was monitored by thin-layer chromatography (35% CHCl$_3$/hexane, R$_f$=0.33). Once the consumption of 2-bromoanthraquinone 10 stopped entirely (it was never fully consumed), the volatiles were removed by rotary evaporation. 3 M HCl was slowly added to the solution until bubbling ceased, then additional 3 M HCl (30 mL) was added. The solution was heated at reflux for 6 hours, turning into an opaque, yellow suspension in the process. The mixture was cooled to room temperature, turning into a transparent solution containing yellow-brown crystals. The contents underwent rotary evaporation as much water as possible. The contents were then vacuum-filtered and washed using deionized water to remove any water, acid and ionic salt, leaving behind a yellow-brown colored solid. The vacuum-filtration receiving flask was changed and the solid was washed with CH$_2$Cl$_2$ through the filter paper. The CH$_2$Cl$_2$ was removed through rotary evaporation. The remaining solid was purified through column chromatography (100% hexane, R$_f$=0.27), providing 2-bromoanthracene 11 as a white, powdery solid (2.00 g, 26%). $^1$H NMR (CDCl$_3$): δ 8.42 (s, 1H), 8.34 (s, 1H), 8.18 (d, 1H), 8.01 (m, 2H), 7.87 (d, 1H), 7.50 (m, 3H).

2-Bromo-9,10-dihydro-9,10-ethanoanthracene-11,12-diol cyclic carbonate (12):

2-Bromoanthracene 11 (2.05 g, 8.0 mmol, 1 equiv.) and vinylene carbonate (3.68 mL, 5.00 g, 58 mmol, 7.3 equiv.) were heated under reflux with stirring for 18 hours, slowly forming a dark brown solution. The consumption of 11 was monitored by thin-layer chromatography (2% CH$_2$Cl$_2$/hexane, R$_f$=0.31). The mixture underwent rotary evaporation under high vacuum to remove the excess vinylene carbonate, providing the cyclic carbonate intermediate 12 as a light-brown solid (2.74 g, >99%). $^1$H NMR (CDCl$_3$): δ 7.52 (dd, 1H), 7.37 (m, 3H), 7.27 (m, 3H), 4.88 (m, 2H), 4.66 (m, 2H).

2-Bromo-9,10-dihydro-9,10-ethanoanthracene-11,12-diol (12a):

Solid potassium hydroxide (1.80 g, 32.0 mmol, 4 equiv.), deionized water (30 mL), and absolute ethanol (3.2 mL) were added to the light-brown cyclic carbonate intermediate 12 (2.74 g, 8.0 mmol, 1 equiv.). The solution was stirred at 75° C. for 3 hours. The consumption of the cyclic carbonate intermediate 12 was monitored through thin-layer chromatography (100% CH$_2$Cl$_2$, R$_f$=0.30). Afterwards, the solution underwent rotary evaporation under reduced pressure to remove the ethanol and roughly half of the water volume. Additional water (60 mL) was added to the solution and the solution was stirred at room temperature for one hour, resulting in the formation of light-tan solid. The contents were vacuum-filtered and then washed with deionized water. The vacuum-filtration receiving flask was changed and the solid was washed with ethyl acetate through the filter paper. The ethyl acetate was removed through rotary evaporation, leaving a white solid residue. The product was purified through column chromatography (90% CH$_2$Cl$_2$/ethyl acetate, R$_f$=0.30 & R$_f$=0.15), providing two isomers of diol intermediate 12a as a white solid (2.01 g, 79%). $^1$H NMR (CDCl$_3$): δ 7.52 (d, 1H), 7.35 (dd, 1H), 7.31 (dd, 2H), 7.25 (d, 1H), 7.17 (dd, 2H), 4.40 (dd, 2H), 4.07 (m, 2H). $^1$H NMR (CDCl$_3$): δ 7.45 (d, 1H), 7.34 (dd, 2H), 7.27 (dd, 1H), 7.20 (dd, 2H), 7.16 (d, 1H), 4.35 (dd, 2H), 4.05 (d, 2H).

2-Bromo-9,10-anthracenedialdehyde (13):

Diol intermediate 12a (1.58 g, 5.0 mmol, 1 equiv.) was dissolved in anhydrous acetonitrile (100 mL) and heated to reflux with stirring and formed a transparent, light-tan solution. Lead tetraacetate (4.42 g, 10.0 mmol, 2 equiv.) was added portion-wise to the solution over a period of 5 minutes quickly turning the solution opaque and brown in color. The solution was then stirred at reflux for 4 hours, resulting in the formation of a dark-orange precipitate within the brown solution. The consumption of the diol intermediates were monitored through thin-layer chromatography (80% CH$_2$Cl$_2$/ethyl acetate, R$_f$=0.50 & R$_f$=0.33). After the reaction was complete, the reaction mixture was concentrated via rotary evaporation and gave a burgundy residue. 10% aqueous sodium carbonate (300 mL) was added to the residue, allowing the residue to be suspended in the aqueous solution. The organic contents were extracted from the aqueous layer using dichloromethane. The opaque, yellow organic layer was dried over anhydrous sodium sulfate, filtered, and concentrated to give a yellow-orange solid residue. The residue was purified by column chromatography (20% ethyl acetate/hexane, R$_f$=0.29), providing 2-bromo-9,10-anthracenedialdehyde 13 as an orange solid (1.23 g, 80%). $^1$H NMR (CDCl$_3$): 11.43 (s, 1H), 11.42 (s, 1H), 9.03 (s, 1H), 8.72 (m, 2H), 8.66 (d, 1H), 7.75 (m, 3H).

Advantages of the Present Invention Over Prior Technology.

The novelty or improvement on the earlier systems is that even though compounds 1 and 2 are fluorescent they require excitation in the ultraviolet range (393 nm) and emit in the visible range (410 nm). This requirement is detrimental to biological studies as the UV radiation uses expensive UV lasers, which are costly to maintain and cocl during operation. The new compounds 3 and 4 contain a cyano group which extends the compounds' pi system just enough that these systems are now excited at 405 nm (blue light) and emit at 420 nm (in the visible light range). This improvement in their photophysical properties coupled with their high selectivity in entering cells via the polyamine transport system make these valuable new tools for molecular biologist and cell biologists interested in tracking polyamine uptake phenomena via fluorescence measurements or via confocal microscopy.

While there are numerous biological stains for tracking or labeling cellular organelles, there are no commercial stains or fluorescent agents that specifically enter and traffic through the cell membrane via the polyamine transport system. The novel compounds herein disclosed can be used to study polyamine transport processes in living cells and to track potential therapeutic agents tagged thereon. Accordingly, advantages of the disclosed compounds include their special PAT targeting ability and their desirable photophysical properties.

These compounds, as cellular stains, are further useful added to cancer cells to track how the cancers are trafficking their polyamine growth factors. These agents may also serve as trackable anticancer drug candidates as they are cell selective for active PATs and are cytotoxic at μM concentrations. As shown in FIGS. 2 and 3, the probes are able to discern between PAT-active and PAT-inactive cell lines (blue halo vs dots, respectively).

Prior to the present disclosure there were no commercial stains or fluorescent agents that specifically enter cells and traffic through the polyamine transport system. This is likely a multi-step process and is likely a time dependent phenomenon. We see an initial sequestration of compound 3 into vesicles followed by escape to reach the perinuclear compartment.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A fluorescent cyano-substituted anthracene polyamine compound according to formula 3

Formula 3

2. The compound of claim 1 used in manufacturing a pharmaceutically acceptable composition.

3. The compound of claim 1 used in a method of treatment by being administered to a patient.

4. The compound of claim 1 used in a method of treatment by being administered to a patient in an amount effective to inhibit a cancer cell.

5. A fluorescent derivative of the compound of claim 1, the derivative according to formula 4

Formula 4

6. The compound of claim 5 used in manufacturing a pharmaceutically acceptable composition.

7. The compound of claim 5 used in a method of treatment by being administered to a patient.

8. The compound of claim 5 used in a method of treatment by being administered to a patient in an amount effective to inhibit a cancer cell.

* * * * *